US010295531B2

(12) United States Patent
Waga

(10) Patent No.: US 10,295,531 B2
(45) Date of Patent: May 21, 2019

(54) DETECTION INSTRUMENT, AND DETECTION SYSTEM

(71) Applicant: Iwao Waga, Tokyo (JP)

(72) Inventor: Iwao Waga, Tokyo (JP)

(73) Assignee: NEC SOLUTIONS INNOVATORS, LTD., Tokyo (JP)

( * ) Notice: Subject to any disclaimer, the term of this patent is extended or adjusted under 35 U.S.C. 154(b) by 219 days.

(21) Appl. No.: 15/143,763

(22) Filed: May 2, 2016

(65) Prior Publication Data

US 2016/0245798 A1    Aug. 25, 2016

Related U.S. Application Data

(63) Continuation of application No. 13/995,576, filed as application No. PCT/JP2011/079402 on Dec. 19, 2011, now abandoned.

(30) Foreign Application Priority Data

Dec. 20, 2010  (JP) ................................. 2010-283718
Oct. 18, 2011  (JP) ................................. 2011-229162

(51) Int. Cl.
*G01N 21/75*  (2006.01)
*G01N 33/53*  (2006.01)
(Continued)

(52) U.S. Cl.
CPC ........ *G01N 33/5302* (2013.01); *B01L 3/5023* (2013.01); *B01L 3/545* (2013.01);
(Continued)

(58) Field of Classification Search
CPC ......... G01N 33/5302; G01N 33/56911; G01N 33/56983; G01N 33/581; G01N 21/78;
(Continued)

(56) References Cited

U.S. PATENT DOCUMENTS 5,296,688 A    3/1994  Hamilton et al. ............ 235/375
5,902,982 A    5/1999  Lappe
(Continued)

FOREIGN PATENT DOCUMENTS

EP    2083269 A1    7/2009
JP    2001-502794 A    2/2001
(Continued)

OTHER PUBLICATIONS

Zhu et al, "Development of a DNA microarray for authentication of Ginseng Drugs based on 18S rRNA gene sequence" J. Agric. Food Chem. 2008, 56, 3953-3959 (Year: 2008).*
(Continued)

*Primary Examiner* — Dennis White

(57) ABSTRACT

The present invention provides a detection instrument capable of easily detecting an intended detection object without any skilled technique. The detection instrument (1) of the present invention includes a detection portion (12), a detection reagent which develops a color by specifically reacting with a detection object in a sample is placed in the detection portion (12), positional information of the detection reagent in the detection portion (12) is information on the detection object, and color development of the detection reagent can be optically read. It is preferred that a bar code is formed in the detection portion (12), and the detection reagent is placed as a part of the bar code.

10 Claims, 10 Drawing Sheets

(51) Int. Cl.
  *G01N 21/78* (2006.01)
  *G01N 33/58* (2006.01)
  *B01L 3/00* (2006.01)
  *C12Q 1/6823* (2018.01)
  *C12Q 1/6837* (2018.01)
  *G01N 33/569* (2006.01)

(52) U.S. Cl.
  CPC ......... *C12Q 1/6823* (2013.01); *C12Q 1/6837* (2013.01); *G01N 21/78* (2013.01); *G01N 33/56911* (2013.01); *G01N 33/56983* (2013.01); *G01N 33/581* (2013.01); *B01L 2300/021* (2013.01); *B01L 2300/0627* (2013.01)

(58) Field of Classification Search
  CPC ..... C12Q 1/6823; C12Q 1/6837; B01L 3/545; B01L 3/5023; B01L 2300/0627; B01L 2300/021
  See application file for complete search history.

(56) References Cited

U.S. PATENT DOCUMENTS

| | | | |
|---|---|---|---|
| 6,270,724 | B1 | 8/2001 | Woodman |
| 6,770,487 | B2 | 8/2004 | Crosby |
| 7,691,634 | B2 | 4/2010 | Vaillant |
| 9,349,086 | B2 | 5/2016 | Nemet et al. |
| 2002/0072079 | A1 | 6/2002 | Woodman |
| 2003/0113228 | A1 | 6/2003 | Goldsmith |
| 2003/0124738 | A1 | 7/2003 | Crosby |
| 2004/0018640 | A1 | 1/2004 | Goldsmith |
| 2004/0018641 | A1 | 1/2004 | Goldsmith |
| 2004/0248305 | A1 | 12/2004 | Vaillant |
| 2005/0003458 | A1 | 1/2005 | Moore ................ B01J 19/0046 435/7.2 |
| 2005/0164199 | A1* | 7/2005 | Stanzel ................ 435/6.11 |
| 2005/0214865 | A1 | 9/2005 | Lappe |
| 2007/0298436 | A1 | 12/2007 | Lappe |
| 2008/0173712 | A1 | 7/2008 | Nemet et al. |
| 2008/0173718 | A1 | 7/2008 | Ibe ................ G06K 7/10732 235/462.01 |
| 2009/0230182 | A1 | 9/2009 | Nemet et al. |
| 2012/0305637 | A1 | 12/2012 | Nemet et al. |
| 2015/0122880 | A1 | 5/2015 | Nemet et al. |
| 2016/0239781 | A1 | 8/2016 | Nemet et al. |

FOREIGN PATENT DOCUMENTS

| | | | |
|---|---|---|---|
| JP | 2002-504684 | A | 2/2002 |
| JP | 2004-20563 | A | 1/2004 |
| JP | 2004-527755 | A | 9/2004 |
| JP | 2005-30825 | A | 2/2005 |
| JP | 2005-519259 | A | 6/2005 |
| JP | 2007-46933 | A | 2/2007 |
| JP | 2007-212391 | A | 8/2007 |
| JP | 2008181195 | A | 8/2008 |
| JP | 2009-118776 | A | 6/2009 |
| JP | 2009-133712 | A | 6/2009 |
| JP | 2009-537038 | A | 10/2009 |
| JP | 2010194741 | A | 9/2010 |
| JP | 2010-220970 | A | 10/2010 |
| JP | 2010-227048 | A | 10/2010 |
| JP | 2010282325 | A | 12/2010 |
| WO | 2004/038353 | A1 | 5/2004 |
| WO | 2006/048164 | A1 | 5/2006 |
| WO | 2009/123255 | A1 | 10/2009 |
| WO | 2011/016565 | A1 | 2/2011 |

OTHER PUBLICATIONS

Japanese Office Action for JP Application No. 2015-190899 dated Aug. 3, 2016 with English Translation.
Yi Xiao et al., "Catalytic Beacons for the Detection of DNA and Telomerase Activity", J. Am. Chem. Soc. 2004, JACS Communications, vol. 126, No. 24, pp. 7430-7431, Published on Web May 28, 2004.
Juewen Liu et al., "Functional Nucleic Acid Sensors", Chem Rev. May 2009, Department of Chemistry, University of Illinois at Urbana-Champaign, IL, USA, vol. 109, No. 5, pp. 1948-1998, Author manuscript; available in PMC May 1, 2010.
Japanese Office Action for JP Application No. 2012-549800 dated Oct. 6, 2016 with English Translation.
Japanese Office Action for JP Application No. 2012-549800 dated Jun. 30, 2015 with English Translation.
Bockisch Benjamin el al., "Immobilized stem-loop structured probes as conformational switches for enzymatic detection of microbial 16S rRNA", Nucleic Acids Research, Oxford University Press, GB, vol. 33, No. 11, Jan. 1, 2005, pp. E101.1-E101.8, XP002581207, ISSN: 0305-1048, DOI: 10.1093/NAR/GNI101 [retrieved on Jun. 24, 2005], figure 1, the whole document, published online Jun. 24, 2005, cited in EP Search Report.
Yoshida W et al., "Aptameric enzyme subunit for biosensing based on enzymatic activity measurement", Nalytical Chemistry, American Chemical Society, US, vol. 78, No. 10, May 15, 2006, pp. 3296-3303, XP003010513, ISSN: 0003-2700, DOI: 10.1021/AC0602540, the whole document, cited in EP Search Report.
The Extended European Search Report for EP Application No. EP11851713.5 dated Dec. 11, 2014.
Japanese Office Action for JP2012-549800 dated Oct. 31, 2014 with partial English Translation.
Li et al., "Label-Free Colorimetric Detection of Aqueous Mercury Ion (Hg2+) Using Hg2+-Modulated G-Quadruplex-Based DNAzymes", Anal. Chem., 2009, vol. 81, pp. 2144-2149.
Zhu et al., "Development of a DNA Microarray for Authentication of Ginseng Drugs Based on 18S rRNA Gene Sequence", Journal of Agricultural and Food Chemistry, 2008, vol. 56, pp. 3953-3959.
Troein et al., "An Introduction to BioArray Software Environment", Methods in Enzymology, 2006, vol. 411, pp. 99-119.
International Search Report of PCT Application No. PCT/JP2011/079402 dated Jan. 24, 2012.

* cited by examiner

DETECTION INSTRUMENT, AND DETECTION SYSTEM

CROSS-REFERENCE TO RELATED APPLICATIONS

The present application is a continuation application of U.S. patent application Ser. No. 13/995,576 filed on Jun. 19, 2013, which is a National Stage Entry of International Application PCT/JP2011/079402, filed on Dec. 19, 2011, which claims the benefit of priority from Japanese Patent Application 2010-283718 filed on Dec. 20, 2010 and 2011-229162 filed on Oct. 18, 2011, the disclosures of all of which are incorporated in their entirety by reference herein.

TECHNICAL FIELD

The present invention relates to a detection instrument and a detection system.

BACKGROUND ART

Recently, cases involving food such as misrepresentation cases and pesticide contamination cases have occurred. Further, cases of food poisoning caused by microorganisms such as an *Escherichia coli* O157 strain and *Salmonella enterica*, and food-borne infectious diseases such as a Creutzfeldt-Jakob disease caused by a pathogenic protein and the like have occurred. Furthermore, accompanying the arrival of an aging society, public health consciousness is spreading. Because of this, public awareness on food is high, and safe and healthy food is required. In order to ensure the quality of food, a system for inspecting the quality of food is necessary in a food production stage, a food distribution stage, and a food consumption stage. On the other hand, as a method for specifically detecting a specific substance, there is a method utilizing an antigen-antibody reaction. For example, the patent document 1 discloses a method for inspecting components in food, using an antigen-antibody reaction.

PRIOR ART DOCUMENTS

Patent Document

Patent Document 1: JP 2009-133712 A

SUMMARY OF INVENTION

Problem to be Solved by the Invention

Sanitation inspections and contamination inspections are carried out in the food production stage because of the requirement by the food sanitation law and the voluntary management by food companies and the like. However, skilled techniques are required in order to carry out these inspections of food quality. Therefore, it is rare that food quality is inspected in a distribution stage and a consumption stage. That is, it is impossible to inspect food quality by part-time workers having no skilled technique in supermarkets, department stores, convenience stores, and restaurants in the same manner as in food factories. The same applies to inspections of chemical substances such as pesticides in a food production stage. It is required to remove such difficulties in inspections not only in the food field, but also in all of fields relating to public health such as the medical field and the agricultural field.

Hence, the present invention is intended to provide a detection instrument and a detection system, capable of easily detecting an intended detection object without any skilled technique.

Means for Solving Problem

The detection instrument according to the present invention is a detection instrument including: a detection portion, wherein a detection reagent which develops a color by specifically reacting with a detection object in a sample is placed in the detection portion, positional information of the detection reagent in the detection portion is information on the detection object, and color development of the detection reagent can be optically read.

The detection system according to the present invention is a detection system including: the detection instrument according to the present invention; and an optical reader, wherein the detection object is detected by reading color development of the detection reagent in the detection instrument by the optical reader.

Effects of the Invention

The present invention uses an easy method of optically reading color development of a detection reagent. Thus, according to the present invention, everyone can easily detect an intended detection object without any skilled technique.

BRIEF DESCRIPTION OF DRAWINGS

FIGS. 6A and 6B show a specific example of the detection method in Embodiment 1-1a.

DESCRIPTION OF EMBODIMENTS

In the present invention, the concept of "color development" encompasses coloring. In the present invention, the concept of "detection" encompasses quantitative analysis, semi-quantitative analysis, and qualitative analysis.

The embodiments of the present invention are described. The present invention, however, is not limited by the following embodiments.

(Embodiment 1)

Figure 1A:
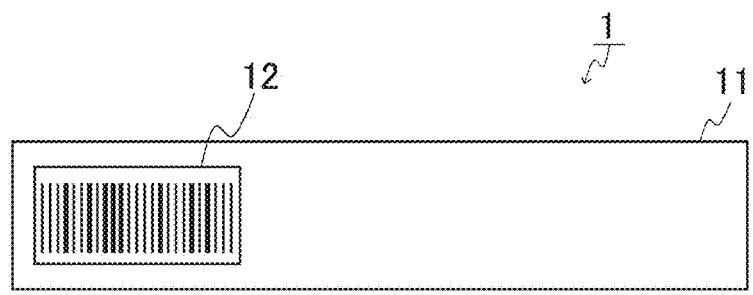
FIG. 1A is a plan view showing an example of a configuration of a detection instrument of Embodiment 1 according to the present invention.

FIG. 1A shows an example of a configuration of a detection instrument according to the present invention. As shown in FIG. 1A, this detection instrument 1 is configured so that a detection portion 12 is formed in a main body 11. A detection reagent which develops a color by specifically reacting with a detection object in a sample is placed in the detection portion 12. In the detection portion 12, positional information of the detection reagent is information on the detection object.

It is preferred that a bar code is formed in the detection portion 12 of the detection instrument according to the present invention as shown in FIG. 1A, and the detection reagent is placed as a part of the bar code. The detection portion (bar code) 12 may include, besides information on the detection object, information such as information on the detection reagent (information on the kind of the detection reagent and the like) other than the positional information and information on a site at which detection is performed using the detection information, for example. With this embodiment, it is possible to detect the detection object with reference to information on the kind of the detection reagent, information on the site at which detection is performed, and the like. The bar code is not limited to a one-dimensional code shown in FIG. 1A and may be, for example, a two-dimensional code such as a QR code (registered trademark) shown in FIG. 1B.

The detection instrument shown in FIG. 1A can be produced by forming a detection portion (bar code) 12 in a main body 11 of a detection instrument 1. A method for forming the detection portion (bar code) 12 is not particularly limited and can be, for example, a method such as printing using a printer such as an ink-jet recording device or a laser printer. In this case, for example, by causing the detection reagent to be contained in an ink or a toner at the time of printing a part of the detection portion (bar code) 12, the detection reagent is placed as the part of the detection portion (bar code) 12.

The detection reagent is not particularly limited as long as it develops a color by specifically reacting with a detection object in a sample, and examples thereof include a nucleic acid element described below, an antibody, and an antigen.

The method for using the detection instrument shown in FIG. 1A is, for example, as follows. Note here that the following method is a mere example, and the present invention is not limited by this.

First, the detection portion (bar code) 12 is brought into contact with a sample. At that time, when a detection object is present in the sample, the detection reagent specifically reacts with the detection object and thus develops a color.

In the present invention, the sample is not particularly limited, and examples thereof include food (including beverages), pharmaceuticals, chemicals, the ground, animals, plants, microorganisms, virus, water (e.g., tap water, discharged water, river water, seawater, rainwater, and snow), garbage, and waste.

In the present invention, the detection object is not particularly limited, and examples thereof include high-molecular compounds, low-molecular compounds, organic substances, and inorganic substances. Examples of the high-molecular compounds or the organic substances include microorganisms, virus, polysaccharides, proteins, nucleic acids, and resins. Examples of the low-molecule compounds include pesticides, pharmaceuticals, chemicals, oligosaccharides, monosaccharides, lipids, oligopeptides, amino acids, vitamins, and bioactive substances. Examples of the inorganic substances include minerals, mineral acids, and metals.

Figure 1B:
FIG. 1B is a plan view showing another example of a configuration of a detection instrument of Embodiment 1 according to the present invention.
Figure 2A:
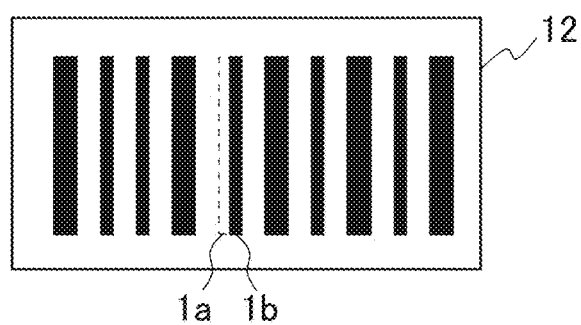
FIGS. 2A and 2B are plan views illustrating an example of detection of a detection object in a detection portion of the detection instrument of Embodiment 1.
Figure 2B:
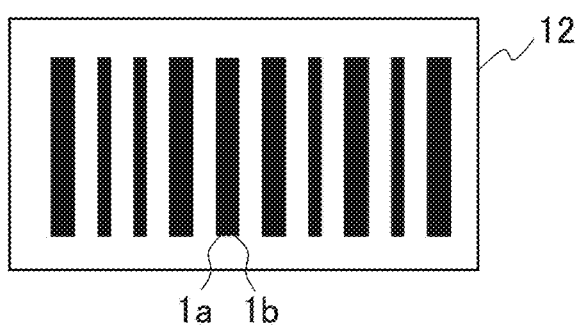

An example of detecting the detection object in the detection portion is described with reference to FIGS. 2A and 2B. In FIGS. 2A and 2B, the identical parts to those in FIGS. 1A and 1B are denoted by identical reference numerals. In FIG. 2A, a bar code is formed in the detection portion 12, and a detection reagent 1a is placed as a part of the bar code. In the detection portion (bar code) 12, positional information of the detection reagent 1a is information on the detection object. The detection reagent 1a is placed adjacent to a bar 1b in the detection portion (bar code) 12. At the time when a sample is brought into contact with the detection portion (bar code) 12, when the detection object is present in the sample, the detection reagent 1a placed adjacent to the bar 1b specifically reacts with the detection object and develops a color as shown in FIG. 2B. For example, when the detection object is an *Escherichia coli* O157 strain, a detection reagent which develops a color by contact with an *Escherichia coli* O157 strain is used as the detection reagent 1a. As described above, when the detection object is present in the sample, the thickness of the bar 1b is increased by color development of the detection reagent 1a as shown in FIG. 2B. On the other hand, when the detection object is not present in the sample, the bar 1b is thin as it is (in the state shown in FIG. 2A). Whether or not the thickness of the bar 1b is increased is read by a bar-code reader and detected.

Figure 3A:
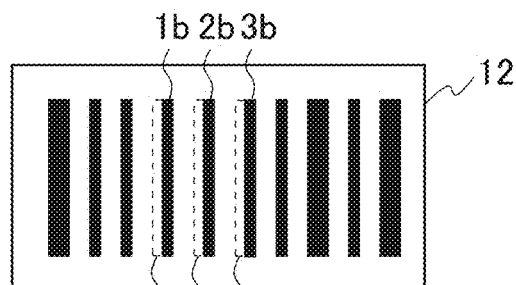
FIGS. 3A to 3D are plan views showing another example of detection of a detection object in a detection portion of the detection instrument of Embodiment 1.
Figure 3B:
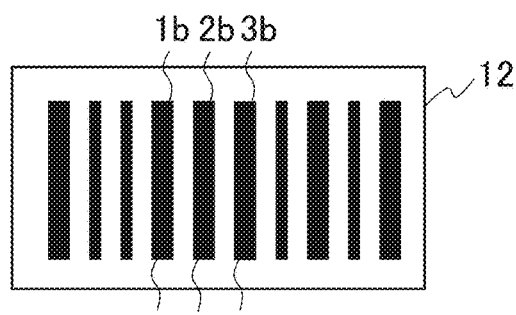
Figure 3C:
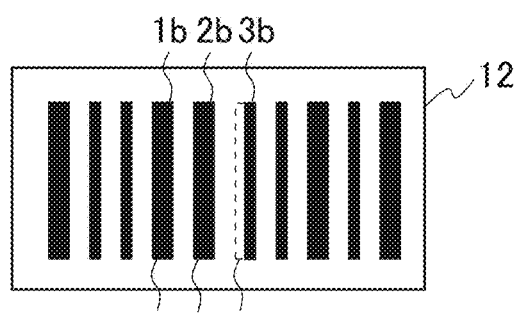
Figure 3D:
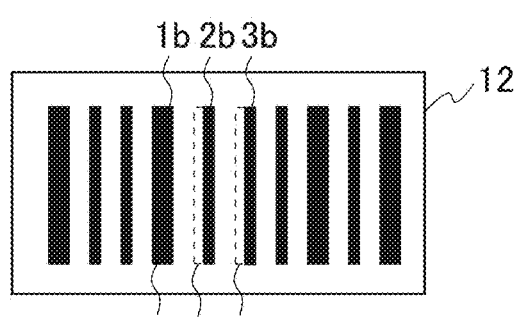

Another example of detection of the detection object in the detection portion is described with reference to FIGS. 3A to 3D. In FIGS. 3A to 3D, the identical parts to those in FIGS. 1A to 2B are denoted by identical reference numerals. In FIG. 3A, a bar code is formed in the detection portion 12, and three detection reagents 1a, 2a, and 3a are placed as parts of the bar code. For example, a detection reagent for an *Escherichia coli* O157 strain as the detection reagent 1a, a detection reagent for *Salmonella enterica* as the detection reagent 2a, a detection reagent for *Staphylococcus* as the detection reagent 3a are placed. In the detection portion (bar code) 12, three pieces of positional information of the detection reagents 1a, 2a, and 3a are the respective pieces of information on the three detection objects (*Escherichia coli* O157 strain, *Salmonella enterica*, and *Staphylococcus*). The detection reagents 1a, 2a, and 3a are placed adjacent to the respective bars 1b, 2b, and 3b in the detection portion (bar code) 12. At the time when a sample is brought into contact with the detection portion (bar code) 12, when all of *Escherichia coli* O157 strain, *Salmonella enterica*, and *Staphylococcus* are present in the sample, the three detection reagents 1a, 2a, and 3a specifically react with the respective three detection objects (*Escherichia coli* O157 strain, *Salmonella enterica*, and *Staphylococcus*) and develop a color as shown in FIG. 3B. When an *Escherichia coli* O157 strain and *Salmonella enterica* are present in the sample, two detection reagents 1*a* and 2*a* specifically react with the respective two detection objects (*Escherichia coli* O157 strain and *Salmonella enterica*) and develop a color as shown in FIG. 3C. When only an *Escherichia coli* O157 strain is present in the sample, the detection reagent 1*a* specifically reacts with the detection object (*Escherichia coli* O157 strain) and develops a color as shown in FIG. 3D. As described above, when any of the three detection objects (an *Escherichia coli* O157 strain, *Salmonella enterica*, and *Staphylococcus*) is present in the sample, the thickness of a corresponding bar among the bars 1*b*, 2*b*, and 3*b* is increased as shown in FIGS. 3B to 3D. On the other hand, when none of the three detection objects (an *Escherichia coli* O157 strain, *Salmonella enterica*, and *Staphylococcus*) is present in the sample, the bars 1*b*, 2*b*, and 3*b* are thin as they are (in the state shown in FIG. 3A). Then, whether or not any of the thicknesses of the bars 1*b*, 2*b*, and 3*b* is increased is read by a bar-code reader and detected. In FIGS. 3A to 3D, the number of detection reagents is set to three, and the number of detection reagents, however, can be increased or decreased if necessary. With this configuration, a plurality of detection objects can be detected simultaneously.

Figure 4A:
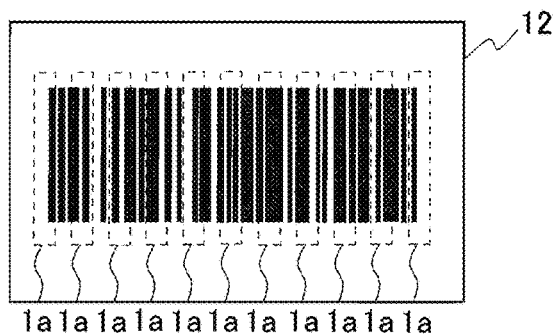
FIGS. 4A to 4D are plan views showing yet another example of detection of a detection object in a detection portion of the detection instrument of Embodiment 1.
Figure 4B:
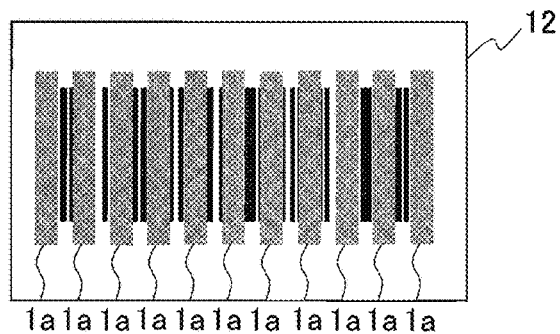
Figure 4C:
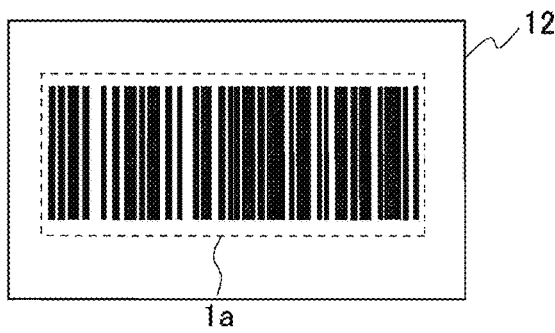
Figure 4D:
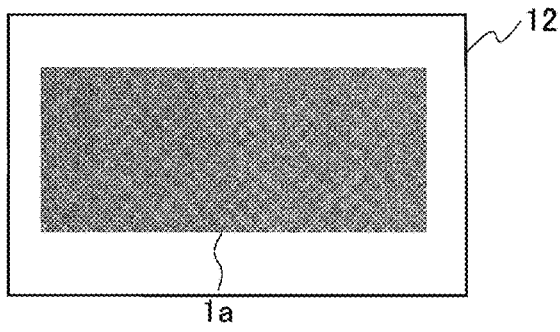

In the detection instrument according to the present invention shown in FIG. 1A, besides the bar code formed in the detection portion 12, the detection reagent may be placed on a part of or the entire bar code, and the part of or the entire bar code may be indistinguishable by color development of the detection reagent. The present embodiment is described with reference to FIGS. 4A to 4D. In FIGS. 4A to 4D, the identical parts to those in FIGS. 1A to 3D are denoted by identical reference numerals. In FIG. 4A, a bar code is formed in a detection portion 12, and besides the bar code, eleven detection reagents 1*a* are placed on the respective parts of the barcode. In the detection portion 12, positional information of the eleven detection reagents 1*a* is information on the detection object. At the time when a sample is brought into contact with the detection portion 12, when the detection object is present in the sample, the detection reagents 1*a* specifically react with the detection object and develop a color as shown in FIG. 4B. For example, in the case where the detection object is an *Escherichia coli* O157 strain, a detection reagent which develops a color by contact with an *Escherichia coli* O157 strain is used as the detection reagents 1*a*. It is checked and detected that a part of the bar code is indistinguishable by color development of the detection reagent 1*a* using a bar-code reader. In FIG. 4C, a bar code is formed in the detection portion 12, and besides the bar code, a detection reagent 1*a* is placed on the entire bar code. In the detection portion 12, positional information of the detection reagent 1*a* is information on the detection object. At the time when a sample is brought into contact with the detection portion 12, when the detection object is present in the sample, the detection reagent 1*a* specifically reacts with the detection object and develops a color as shown in FIG. 4D. For example, in the case where the detection object is an *Escherichia coli* O157 strain, a detection reagent which develops a color by contact with an *Escherichia coli* O157 strain is used as the detection reagent 1*a*. It is checked and detected that the entire bar code is indistinguishable by color development of the detection reagent 1*a* using a bar-code reader.

Embodiment (1-1)

The present embodiment is an example of a detection instrument in the case where the detection reagent contains a nucleic acid element. The detection instrument of the present embodiment is a detection instrument wherein the detection reagent contains a nucleic acid element, the nucleic acid element contains a first nucleic acid portion and a second nucleic acid portion, the first nucleic acid portion is a binding portion which can bind to the detection object, the second nucleic acid portion is a labeling portion which can distinguish between binding and non-binding of the first nucleic acid portion and the detection object, and the labeling portion can cause the detection reagent to or not to develop a color according to the distinguishing between the binding and non-binding.

<Nucleic Acid>

In the present embodiment, the kind of the nucleic acid is not particularly limited, and examples thereof include a single strand such as a single-stranded RNA or a single-stranded DNA and a double-stranded nucleic acid such as a double-stranded RNA or a double-stranded DNA. In the present embodiment, the nucleic acids may be used alone or in a combination of two or more of them. The nucleic acid may have a secondary structure formed by self-annealing, for example. The secondary structure can be, for example, a stem-loop structure.

The nucleic acid may have, for example, a naturally-derived nucleic acid sequence or a synthesized nucleic acid sequence. A method for synthesizing the nucleic acid is not at all limited and can be, for example, a method in which a nucleic acid is chemically synthesized from terminal bases using dNTP or the like as a material by a DNA synthesizer or an RNA synthesizer. Examples of the nucleic acid include DNA and RNA as mentioned above. The nucleic acid may contain peptide nucleic acid such as PNA, for example. The nucleic acid may contain a natural nucleic acid (nonartificial nucleic acid) such as A, C, G, T, or U or may contain an artificial nucleic acid such as 2'-fluorouracil, 2'-aminouracil, 2'-O-methyluracil, or 2-thiouracil, for example.

In the detection instrument according to the present embodiment, the nucleic acid element preferably is a single-stranded nucleic acid obtained by linking the first nucleic acid portion and the second nucleic acid portion. As described above, when the nucleic acid element is a single-stranded nucleic acid, the secondary structure changes by binding of a detection object to the first nucleic acid portion, and this change is prone to cause a change in secondary structure of the second nucleic acid portion. The present invention, however, is not limited by this, the first nucleic acid portion and the second nucleic acid portion may be linked via a linker.

The nucleic acid preferably is an aptamer, for example. The aptamer generally means a nucleic acid molecule which can specifically bind to a specific target substance.

The aptamer may be, for example, DNA or RNA as mentioned above and may be a single-stranded nucleic acid such as a single-stranded RNA or a single-stranded DNA or a double-stranded nucleic acid such as a double-stranded RNA or a double-stranded DNA. The aptamer may be a naturally-derived nucleic acid sequence or a synthesized nucleic acid sequence and may contain peptide nucleic acid such as PNA, the natural nucleic acid (nonartificial nucleic acid), or the artificial nucleic acid.

A method for producing an aptamer is not particularly limited, and it can be produced by the above-mentioned conventionally known method, for example. As mentioned above, for example, in the case of introducing an aptamer which can bind to a target substance into an animal in the present embodiment, the conventionally known SELEX (Systematic Evolution of Ligands by Exponential Enrichment) method or the like can be employed in the aptamer production, for example.

The preparation of an aptamer by the SELEX method is not particularly limited and can be carried out as follows, for example. First, a nucleic acid pool containing a plurality of nucleic acids is provided. Then, the nucleic acid library and a target substance are bound to (associated with) each other to form complexes between them. Thereafter, only a nucleic acid pool involved in formation of the complexes is collected from the complexes. Thus, nucleic acid aptamers which can specifically bind to the secondary reagent can be prepared. A method for preparing nucleic acid aptamers which can specifically bind to a target substance using the SELEX method is shown below as an example. The present invention, however, is not at all limited by this method.

The nucleic acid pool is, for example, a library (mixture) of nucleic acids each having a random region. Examples of the nucleic acids in the library include polynucleotides such as RNAs and DNAs. The random region is, for example, a region in which bases of A, G, C, and U or bases of A, G, C, and T are randomly linked, and the length thereof is, for example, in the range from 20 to 120 mer. The nucleic acid pool includes preferably from $4^{20}$ to $4^{120}$ types (about from $10^{12}$ to $10^{72}$ types) of nucleic acids, more preferably from $4^{30}$ to $4^{60}$ types (about from $10^{18}$ to $10^{36}$ types) of nucleic acids.

It is only necessary that each of the polynucleotides contained in the nucleic acid pool has the random region, for example, and the other configuration is not particularly limited. It is preferred that each of the polynucleotides has, for example, in addition to the random region, a primer region utilized in nucleic acid amplification described below, a polymerase recognition region that can be recognized by a polymerase, and the like, at least one of the 5'-end and 3'-end of the random region. The polymerase recognition region can be decided as appropriate according to the type of polymerase to be used in the nucleic acid amplification described below in preparation of aptamers, for example. In the case where the nucleic acid pool is an RNA pool, the polymerase recognition region is, for example, preferably a DNA-dependent RNA polymerase recognition region (hereinafter, also referred to as an "RNA polymerase recognition region"), and specifically, a T7 promoter that is a T7 RNA polymerase recognition region. A specific example of the RNA pool can be, for example, an RNA pool containing RNAs each having a structure in which, from the 5'-end side thereof, the RNA polymerase recognition region and the primer region (hereinafter, also referred to as a "5'-end side primer region") are linked in this order, the random region is linked to the 3'-end side of the 5'-end side primer region, and the primer region (hereinafter, also referred to as a "3'-end side primer region") is linked to the 3'-end side of the random region. It is preferred that the 5'-end side primer region in the RNA is, for example, a sequence complementary to the 3'-end of a DNA antisense strand synthesized using the RNA as a template, i.e., a sequence that is the same as a sequence of a primer that can bind to the 3'-end of the antisense strand. Moreover, the RNA pool may further include a region that assists the binding to a secondary reagent which is a target substance, for example. Each of the polynucleotides in the nucleic acid pool may have a different random region or a random region a part of which is a common sequence. The respective regions in each of the polynucleotides may be directly adjoined to one another or may be indirectly adjoined through intervening sequences.

A method for preparing the nucleic acid pool is not particularly limited, and a known method can be employed. In the case where the nucleic acid pool is an RNA pool, the nucleic acid pool can be prepared using an initial pool containing DNAs and, as templates, the DNAs, for example. Hereinafter, a DNA strand used as a template of RNAs in a nucleic acid pool is also referred to as an antisense strand, and a DNA strand having a sequence of any of the RNAs with U replaced by T is also referred to as a sense strand. It is preferred that the initial pool containing DNAs contains, for example, any of DNAs (antisense strands) each obtained by replacing U in a strand complementary to each random region in the RNA pool by T and DNAs (sense strands) each having a sequence obtained by replacing U in each random region by T. Nucleic acid amplification is conducted using each of the DNAs in this initial pool as a template and a DNA-dependent DNA polymerase. Thereafter, a transcription reaction is conducted using each of obtained DNA amplification products as a template and a DNA-dependent RNA polymerase. Thus, a nucleic acid pool containing RNAs can be prepared.

It is also possible to prepare a nucleic acid pool containing RNAs by nucleic acid amplification through a preparation of an initial pool containing DNAs each obtained by replacing U in each random region of each of the RNAs by T and annealing of primers each having an RNA polymerase recognition region and a sequence complementary to a 5'-end side primer region, using the initial pool as a template.

Then, the nucleic acid pool and a target react with each other. Thus, a composite of the nucleic acid pool and the target is formed. In the preparation of aptamers, a target substance that reacts with the nucleic acid pool may be, for example, the above-described target substance or a degradate thereof. A binding form between the nucleic acid pool and the target is not particularly limited and can be, for example, binding via intermolecular force such as a hydrogen bond. A treatment for binding the nucleic acid pool and the target substance can be, for example, a method in which the both are incubated for a certain period of time in a solvent. The solvent is not particularly limited and preferably the one can maintain the binding of the both and the like. Examples of the solvent include various buffer solutions.

Subsequently, the composite of the nucleic acid pool and the target is collected. A reaction solution in which the both are caused to react with each other in order to form a composite contains, besides the composite, a nucleic acid pool (hereinafter referred to as an "unreacted nucleic acid pool") that does not involved in formation of the composite, for example. Therefore, for example, it is preferred that the composite and the unreacted nucleic acid pool are separated from the reaction solution. A method for separating the composite and the unreacted nucleic acid pool from each other is not particularly limited and can be, for example, a method utilizing the difference in adsorbability between the target substance and the nucleic acid pool or the difference in molecular weight between the composite and the nucleic acid pool.

As the former method utilizing the difference in adsorbability, the following method is illustrative, for example. That is, first, a carrier having adsorbability to the target substance and the reaction solution containing the composite are brought into contact with each other. At that time, the unreacted nucleic acid pool is not adsorbed to the carrier. In contrast, the composite of the target substance and the nucleic acid pool is adsorbed to the same. Thus, the unreacted nucleic acid pool and the composite can be separated from each other. Therefore the composite adsorbed to the carrier can be collected after removing the unreacted nucleic acid pool. It is preferred that the carrier is washed in order to completely remove the unreacted nucleic acid pool prior to collection of the composite from the carrier, for example. The carrier having adsorbability to the target substance is not particularly limited and can be selected as appropriate according to the type of the target, for example. In the case where the target substance is, for example, a protein such as an antibody, the carrier having adsorbability can be, for example, a nitrocellulose film.

As the latter method utilizing the difference in molecular weight, a method using a carrier can be illustrative, for example. The carrier can be, for example, a carrier having pores each with a pore size with which the nucleic acid pool is allowed to pass therethrough, but the composite is not allowed to pass therethrough. By utilizing such carrier, the composite and the unreacted nucleic acid pool can be separated from each other. The separation may be, for example, electrical separation using an agarose gel, a polyacrylamide gel, or the like.

Besides these methods, a method using a target substance immobilized on a carrier in formation of composite can be used, for example. That is, the target substance is previously immobilized on a carrier, and the carrier and the nucleic acid pool are brought into contact with each other. Thus, a composite of the immobilized target substance and the nucleic acid pool is formed. Then, an unreacted nucleic acid pool binding to no immobilized target substance is removed, and thereafter the composite of the target substance and the nucleic acid pool is dissociated from the carrier. A method for immobilizing the target substance on the carrier is not at all limited, and a known method can be employed. Specifically, the method can be, for example, a method in which the target substance is previously bound to a label, and a carrier having a ligand with the label and the target substance binding to the label are brought into contact with each other. The label can be, for example, a His-tag. Examples of the ligand include metal ions such as a nickel ion ($Ni^{2+}$) and a cobalt ion ($Co^{2+}$). Specific examples of the carrier include Ni-agarose and Ni-sepharose based on the metal ions.

Then, a nucleic acid pool involved in formation of the composite is collected from the collected composite. The nucleic acid pool involved in formation of the composite can be collected by releasing a bond between the target substance and the nucleic acid pool, for example.

Subsequently, nucleic acid amplification of the collected nucleic acid pool involved in formation of the composite is conducted. A method for amplifying the nucleic acid pool is not particularly limited, and the nucleic acid pool can be amplified by a known method according to the type of the nucleic acid pool, for example. In the case where the nucleic acid pool is an RNA pool, for example, first, cDNAs are prepared by a reverse transcription reaction using an RNA-dependent DNA polymerase, and nucleic acid amplification of DNAs is conducted by a PCR or the like using the each of the cDNAs as a template. Then, using each of amplification products thus obtained as a template and using, for example, a DNA-dependent RNA polymerase, a transcription of RNAs is conducted. Thus, the RNA pool involved in formation of the composite can be amplified.

When the RNA pool contains an RNA polymerase recognition region, a 5'-end side primer region, a random region, and a 3'-end side primer region, the nucleic acid amplification can be conducted by an amplification method utilizing these regions, for example. In a reverse transcription reaction for preparing the cDNAs using each of the RNAs as a template, it is preferred that a polynucleotide having a sequence complementary to the 3'-end side primer region contained in the RNA pool is used as a primer, for example. Further, in amplification of DNAs using each of the cDNAs as a template, it is preferred that a polynucleotide having the 5'-end side primer region and a polynucleotide having a strand complementary to the 3'-end side primer region are used as primers, for example. It is preferred that the former polynucleotide further has the RNA polymerase recognition region on the 5'-end side thereof and the 5'-end side primer region on the 3' side thereof, for example. In amplification of RNAs using each of obtained amplification products of DNAs as a template, nucleic acid amplification such as a PCR is conducted using each of the DNA amplification products as a template, a 5'-end side primer region and the 3'-end side primer region in each of the DNAs, and a DNA-dependent DNA polymerase. In this case, for example, it is preferred that a polynucleotide containing the 5'-end side primer region and a polynucleotide containing a strand complementary to the 3'-end side primer region are used as primers. It is preferred that the former polynucleotide has the RNA polymerase recognition region on the 5'-end side thereof and the 5'-end side primer region on the 3' side thereof, for example. Then, a transcription reaction in vitro is conducted using each of obtained amplification products as a template, the RNA polymerase recognition region in each of the amplification products, and the DNA-dependent RNA polymerase. Thus, nucleic acid amplification of the RNA pool involved in formation of the composite can be conducted. In each of the amplification products, a DNA of an antisense strand has an RNA polymerase recognition region on the 3'-end side thereof, for example. Therefore, the DNA-dependent RNA polymerase is bound to this region, and each of the RNAs can be synthesized using the antisense strand as a template. The RNA-dependent DNA polymerase used in the reverse transcription reaction is not particularly limited, and a reverse transcriptase derived from avian myeloblastosis virus (AMV Reverse Transcriptase) can be used, for example.

The method for amplifying nucleic acid is not particularly limited, and for example, any of a PCR method and various isothermal amplification methods can be employed. The conditions thereof are also not particularly limited.

As described above, a nucleic acid pool forming a composite with a target substance is collected. Further, as mentioned above, formation of composite using a target substance, collection of the composite, separation of a nucleic acid pool involved in formation of the composite, amplification of the separated nucleic acid pool, and the like are repeated. Thus, nucleic acid aptamers having binding properties to the target substance can be eventually obtained.

<Form of Nucleic Acid Element>

Examples of the nucleic acid element in the present embodiment include the following two forms (1) and (2):
(1) a nucleic acid element in which the second nucleic acid portion can bind to a labeling substance when a detection object binds to the first nucleic acid portion, and the second nucleic acid portion cannot bind to the labeling substance when a detection object binds to the first nucleic acid portion; and
(2) a nucleic acid element in which the second nucleic acid portion can cause an enzyme reaction, the enzyme reaction with the second nucleic acid portion is inhibited when a detection object does not bind to the first nuclei acid portion, and the enzyme reaction is released from being inhibited when a detection object binds to the first nucleic acid portion.

In the form (1), the "labeling substance" is an optional component of the nucleic acid element of the present embodiment.

The form (1) may be the one in which the secondary structure of the second nucleic acid portion changes by binding of the detection object and the first nucleic acid portion, and by the change in the secondary structure, the labeling substance binding to the second nucleic acid portion is released from the second nucleic acid portion. In this case, the form may be the one in which the labeling substance is an enzyme, and an enzyme reaction with the enzyme is inhibited when the enzyme binds to the second nucleic acid portion, and the enzyme reaction is released from being inhibited when the enzyme is released from the second nucleic acid portion.

Embodiment (1-1a)

Figure 5A:
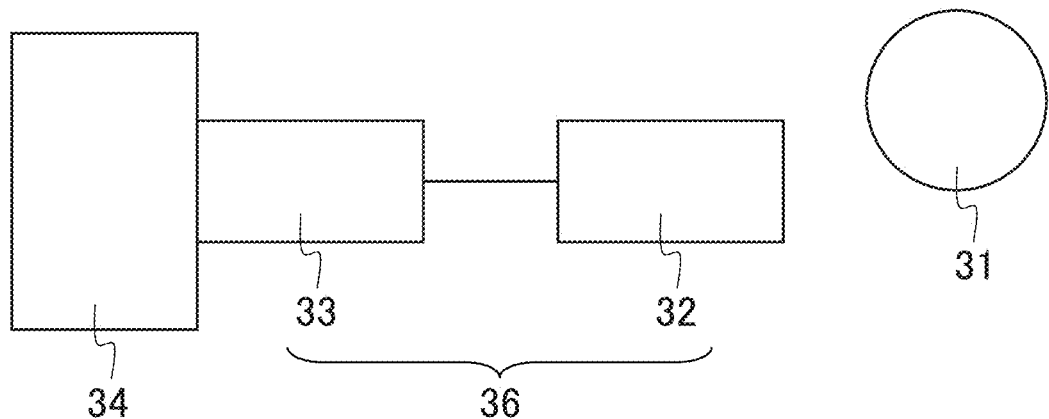
FIGS. 5A and 5B are diagrams schematically showing a detection method for detecting a detection object using a detection instrument of Embodiment 1-1a according to the present invention.
Figure 5B:
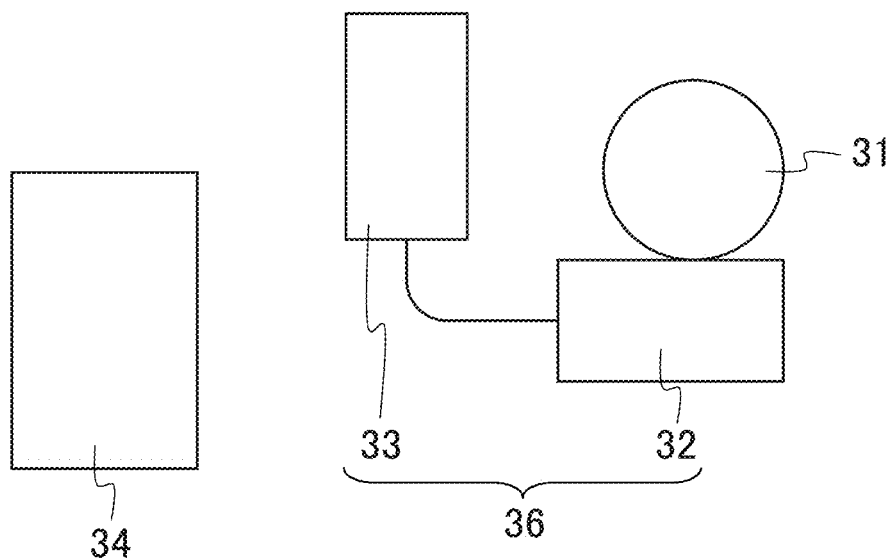

The present embodiment is an example of a detection instrument including a nucleic acid element in the form (1). FIGS. 5A and 5B schematically shows a configuration of the nucleic acid element of the present embodiment. As shown in FIGS. 5A and 5B, this nucleic acid element 36 includes a first nucleic acid portion (binding portion) 32 and a second nucleic acid portion (labeling portion) 33, and the first nucleic acid portion 32 and the second nucleic acid portion 33 are integrated by linking to each other. As shown in FIG. 5A, when a detection object 31 does not bind to the first nucleic acid portion 32, a labeling substance (e.g., enzyme) 34 binds to the second nucleic acid portion 33. Then, as shown in FIG. 5B, when the detection object 31 is present in a sample and binds to the first nucleic acid portion 32, the structure of the second nucleic acid portion 33 changes, resulting in releasing the labeling substance 34 from the second nucleic acid portion 33. In this case, the labeling substance 34 is an enzyme, the enzyme reaction inhibited by binding the enzyme to the second nucleic acid portion 33 is released from being inhibited by releasing the enzyme from the second nucleic acid portion 33. At that time, when a substrate is present, an enzyme reaction occurs. Thus, the detection object can be detected by detecting this enzyme reaction.

In the first nucleic acid portion and the second nucleic acid portion, the length of each nucleic acid is not particularly limited. The lower limit of the length in each of the first nucleic acid portion and the second nucleic acid portion is not particularly limited and is, for example, 7 bases. The upper limit of the same is not particularly limited and is, for example, 120 bases, preferably 80 bases, more preferably 35 bases, yet more preferably 20 bases, and the shorter the length the more preferable. The range of the length in the first nucleic acid portion is, for example, from 7 to 120 bases, preferably from 7 to 80 bases, more preferably from 7 to 35 bases, yet more preferably from 7 to 20 bases. The upper limit of the length of nucleic acid in the second nucleic acid portion is not particularly limited and is, for example, 120 bases, preferably 80 bases, more preferably 60 bases, yet more preferably 40 bases, particularly preferably 35 bases, and the shorter the length the more preferable. The range of the length in the second nucleic acid portion is, for example, from 7 to 120 bases, preferably from 7 to 80 bases, more preferably from 7 to 60 bases, yet more preferably from 7 to 40 bases, particularly preferably from 7 to 35 bases. The length of nucleic acid in the entire nucleic acid element is not particularly limited, and the range of the length is, for example, from 14 to 240 bases, preferably from 14 to 200 bases, more preferably from 14 to 160 bases, yet more preferably from 14 to 140 bases, particularly preferably from 14 to 75 bases, more particularly preferably from 14 to 55 bases. The length in the first nucleic acid portion may be identical to or different from that in the second nucleic acid portion.

The substrate is not particularly limited, and is, for example, preferably a chromogenic substrate that develops a color by an enzyme reaction because it allows detection to be carried out easily. In this case, examples of the enzyme include oxidoreductase and phosphatase. The oxidoreductase can be, for example, peroxidase. The phosphatase can be, for example, alkaline phosphatase. When the enzyme is peroxidase, examples of the chromogenic substrate includes 3,3',5,5'-tetramethylbenzidine (TMB), 1,2-phenylenediamine (OPD), 2,2'-azinobis (3-ethylbenzothiazoline-6-sulfonic acid ammonium salt (ABTS), 3,3'-diaminobenzidine (DAB), 3,3'-diaminobenzidine tetrahydrochloride hydrate (DAB4HCl), 3-amino-9-ethylcarbazole (AEC), 4-chloro-1-naphthol (4C1N), 2,4,6-tribromo-3-hydroxybenzoic acid, 2,4-dichlorophenol, 4-aminoantipyrine, and 4-aminoantipyrine hydrochloride. When the enzyme is alkaline phosphatase, examples of the chromogenic substrate include 5-bromo-4-chloro-3-indolylphosphate/nitrotetrazolium blue (Nitro-TB), and nitro-blue tetrazolium chloride (NBT).

Figure 6A:
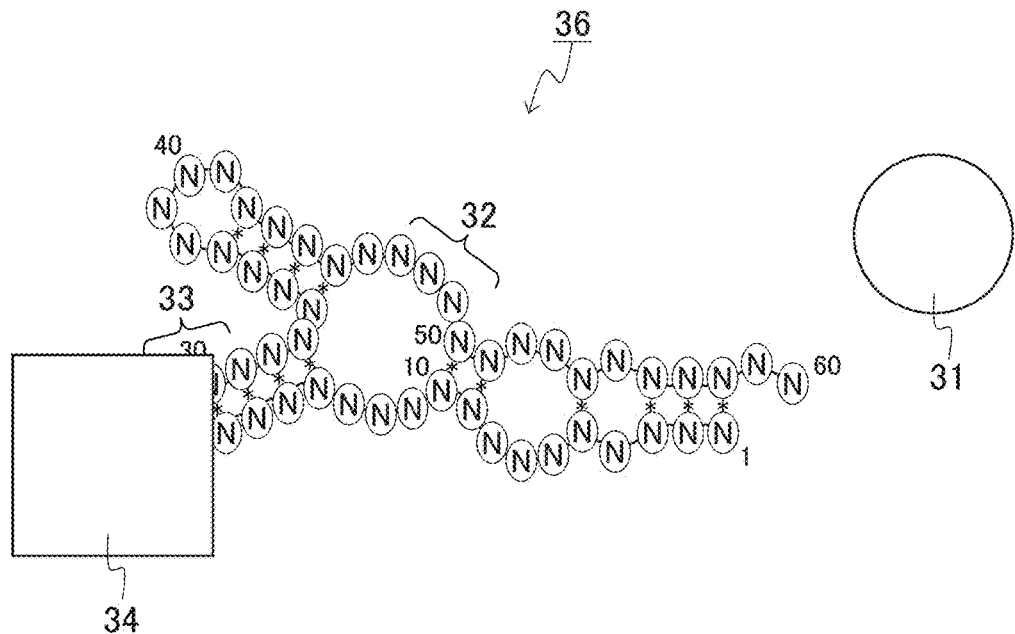
Figure 6B:
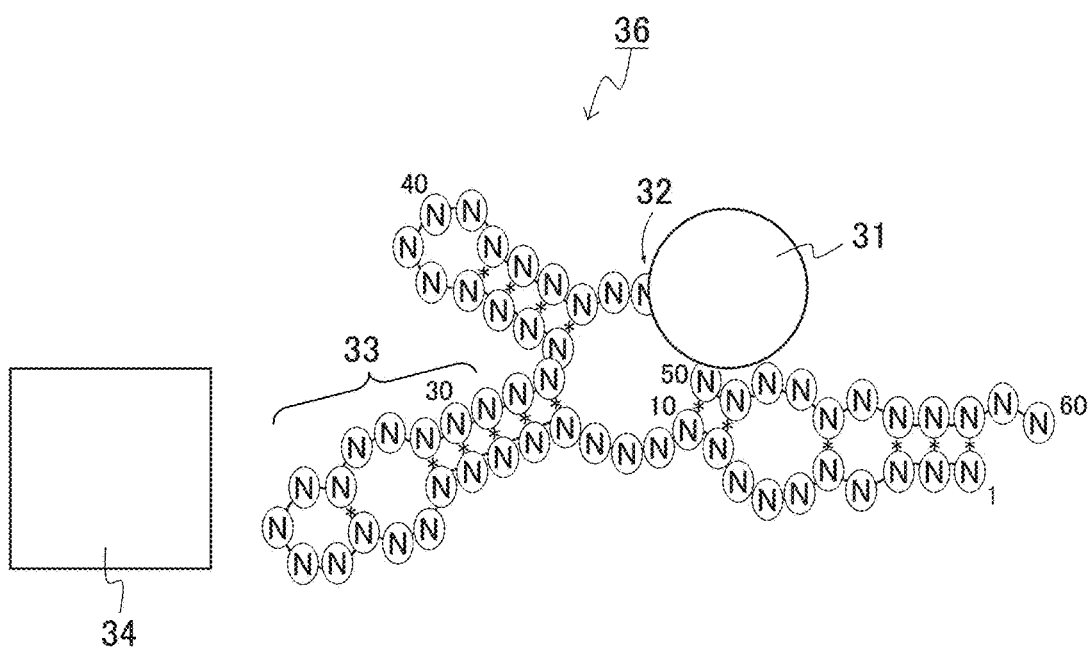

Next, FIGS. 6A and 6B show an example of a nucleic acid element 36 in which aptamers are employed as a first nucleic acid portion 32 and a second nucleic acid portion 33. In FIGS. 6A and 6B, the identical parts to those in FIGS. 5A and 5B are denoted by identical reference numerals. In this nucleic acid element 36, the aptamer as the first nucleic acid portion 32 and the aptamer as the second nucleic acid portion 33 bind to each other to form a single-stranded nucleic acid (RNA). As shown in FIG. 6A, when a detection object 31 does not bind to the aptamer being the first nucleic acid portion 32, a labeling substance (e.g., enzyme) 34 binds to the aptamer being the second nucleic acid portion 33. Then, as shown in FIG. 6B, when the detection object 31 is present in a sample and binds to the aptamer being the first nucleic acid portion 32, the structure of the aptamer as the second nucleic acid portion 33 changes, resulting in releasing the labeling substance 34 from the second nucleic acid portion 33. In this case, the labeling substance 34 is an enzyme, and an enzyme reaction inhibited by binding of the enzyme to the second nucleic acid portion 33 is released from being inhibited by releasing the enzyme from the second nucleic acid portion 33. At that time, when a substrate is present, an enzyme reaction occurs. Thus, the detection object 31 can be detected by detecting this enzyme reaction. Note here that FIGS. 6A and 6B are a mere example, and as long as the second nucleic acid portion 33 can bind to the labeling substance 34 when the detection object 31 does not bind to the first nucleic acid portion 32, and the second nucleic acid portion 33 cannot bind to the labeling substance 34 when the detection object 31 binds to the first nucleic acid portion 32, the other configuration of the nucleic acid element 36 is not particularly limited.

The nucleic acid element including aptamers described above can be produced as follows, for example. First, an aptamer as a first nucleic acid portion is obtained using a detection object as a target. An aptamer as a second nucleic acid portion is obtained using a labeling substance (e.g., enzyme) as a target. The above-mentioned SELEX method can be employed as a method for obtaining the aptamers. Then, these two aptamers are caused to bind to each other. A method for binding these aptamers is not particularly limited and can be, for example, a method in which a single-stranded nucleic acid sequence is produced from sequences of the two aptamers, and a nucleic acid is synthesized based on this single-stranded nucleic acid sequence. In this case, the secondary structures of the two aptamers may be predicted using a computer or the like, and the single-stranded nucleic acid sequence may be revised, or a sequence may be deleted or added to the single-stranded nucleic acid sequence.

Embodiment (1-1b)

Figure 7A:
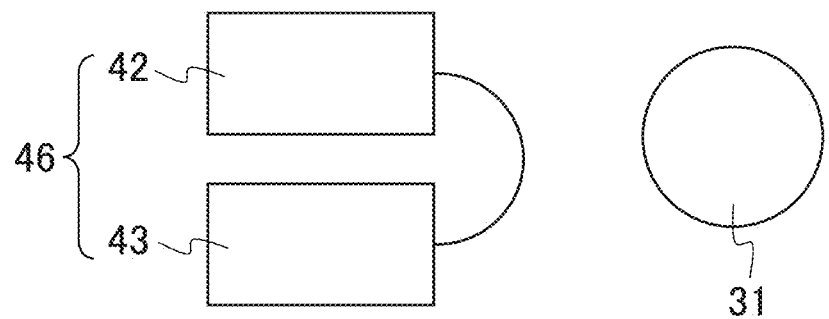
FIGS. 7A and 7B are diagrams schematically showing a detection method for detecting a detection object using a detection instrument of Embodiment 1-1b according to the present invention.
Figure 7B:
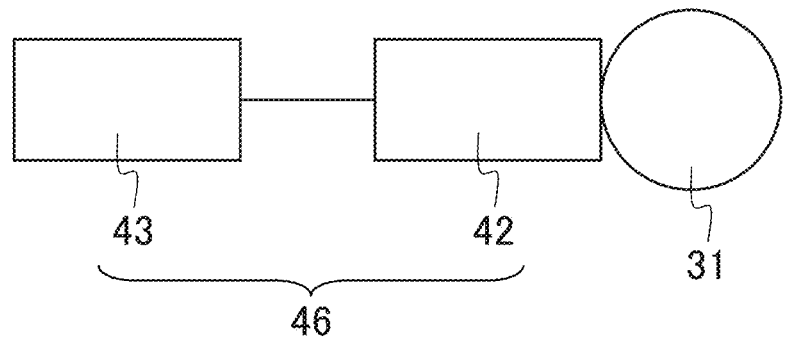

The present embodiment is an example of a detection instrument including a detection reagent which contains a nucleic acid element in the form (2). The nucleic acid element in the form (2) is characterized in that a second nucleic acid portion itself can cause an enzyme reaction. FIGS. 7A and 7B schematically shows a configuration of the nucleic acid element of the present embodiment. As shown in FIGS. 7A and 7B, this nucleic acid element 46 includes a first nucleic acid portion (binding portion) 42 and a second nucleic acid portion (labeling portion) 43, and the first nucleic acid portion 42 and the second nucleic acid portion 43 are integrated by linking to each other. As shown in FIG. 7A, when a detection object 31 does not bind to the first nucleic acid portion 42, the second nucleic acid portion 43 is associated with the first nucleic acid portion 42, resulting in the state of inhibiting an enzyme reaction. Then, as shown in FIG. 7B, when the detection object is present in a sample, and the detection object 31 binds to the first nucleic acid portion 42, the second nucleic acid portion 43 is released from the first nucleic acid portion 42, and thus, the second nucleic acid portion 43 can cause an enzyme reaction. At that time, when a substrate is present, an enzyme reaction occurs. Thus, the detection object 31 can be detected by detecting this enzyme reaction as in the case of Embodiment 1-1a.

In the first nucleic acid portion and the second nucleic acid portion, the length of nucleic acid is not particularly limited. The length of nucleic acid in each of the first nucleic acid portion and the second nucleic acid portion is, for example, the same as that in Embodiment 1-1a. The length of nucleic acid in the entire nucleic acid element is not particularly limited, and the range of the length is, for example, from 14 to 240 bases, preferably from 14 to 200 bases, more preferably from 14 to 160 bases, yet more preferably from 14 to 140 bases, particularly preferably from 14 to 75 bases, more particularly preferably from 14 to 55 bases.

The type of the enzyme reaction of the second nucleic acid portion 43 is not particularly limited and can be, for example, the same enzyme reaction as in Embodiment 1-1a. A nucleic acid which can cause an enzyme reaction can be DNA having Hemin peroxidase activity (Tao et al, Anal. chem. 2009, 81, 2144-2149). The substrate also is not particularly limited and can be, for example, the same substrate as in Embodiment 1-1a.

Figure 8A:
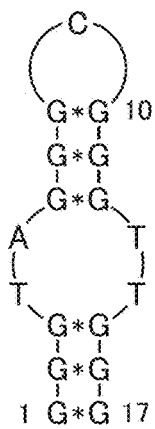
FIGS. 8A to 8D show a specific example of the detection method in Embodiment 1-1b.
Figure 8B:
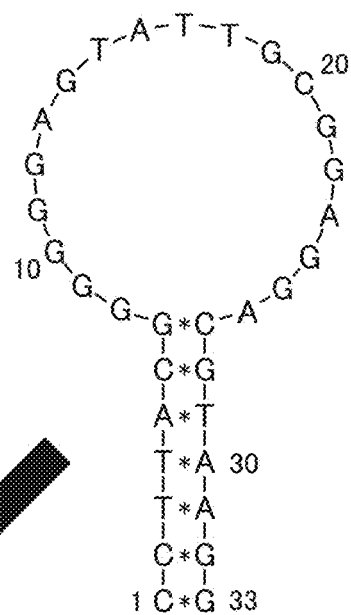
Figure 8C:
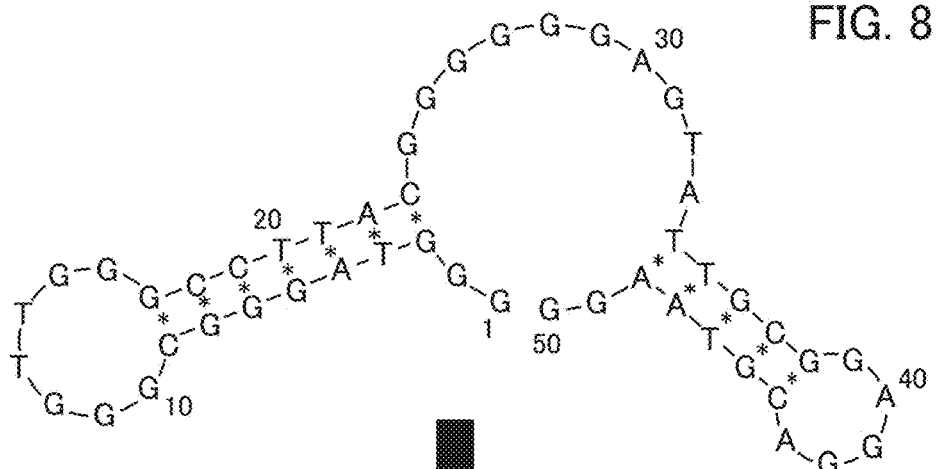
Figure 8D:
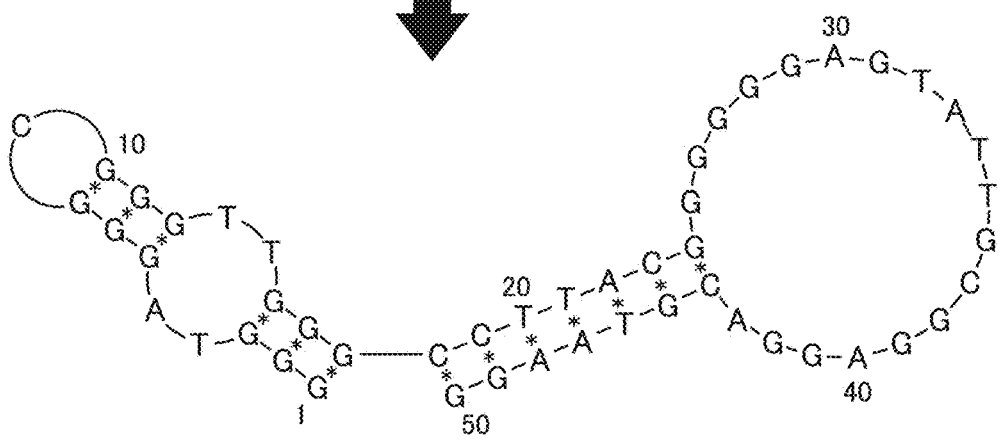

Next, FIGS. 8A to 8D show an example of a nucleic acid element in which an aptamer is employed as a first nucleic acid portion 42, and DNA having peroxidase activity is employed as a second nucleic acid portion 43. FIG. 8A shows DNA having peroxidase activity (SEQ ID NO: 1), and FIG. 8B shows an aptamer to adenosine (SEQ ID NO: 2). FIG. 8C shows a nucleic acid element of a single-stranded nucleic acid obtained by binding the DNA (A) and the aptamer (B) (SEQ ID NO: 3). In the nucleic acid element of FIG. 8C, the aptamer (B) does not bind to adenosine, so that the DNA has a secondary structure which cannot cause an enzyme reaction. Then, when the adenosine binds to the aptamer (B) in the nucleic acid element, the secondary structure of the DNA of FIG. 8C changes to the one which can cause an enzyme reaction as shown in FIG. 8D. At that time, when a substrate is present, an enzyme reaction occurs. Thus, the detection object can be detected by detecting this enzyme reaction. This nucleic acid element can be used in measurement of viable cells in food. That is, the presence of viable cells in food means the presence of ATP, and the concentration of ATP is proportional to the number of viable cells. Therefore, when this nucleic acid element, a chromogenic substrate, and food are caused to react, color development in proportion to the concentration of ATP derived from viable cells can be obtained. Thus, the number of viable cells in food can be detected by detecting this color development.

This nucleic acid element can be produced as follows, for example. First, an aptamer as a first nucleic acid portion is obtained using a detection object as a target. The above-mentioned SELEX method can be employed as a method for obtaining the aptamer. On the other hand, a sequence of a second nucleic acid portion is designed according to an enzyme reaction and synthesized. Then the aptamer as the first nucleic acid portion and the second nucleic acid portion are caused to bind to each other. A method for binding them is not particularly limited and can be, for example, a method in which a single-stranded nucleic acid sequence is produced from a sequence of the aptamer as the first nucleic acid portion and a sequence of the second nucleic acid portion, and a nucleic acid is synthesized based on this single-stranded nucleic acid sequence. In this case, the secondary structures may be predicted using a computer or the like, and the single-stranded nucleic acid sequence may be revised, or a sequence may be deleted or added to the single-stranded nucleic acid sequence.

Embodiment (1-2)

The present embodiment is an example of a detection instrument in which antibodies for capturing a detection object (antigen) are immobilized, as a detection reagent, on the detection portion in the case where the detection object in a sample is a substance which can be an antigen. The antibodies immobilized on the detection portion are not particularly limited as long as they bind to the detection object (antigen) in the sample, and can be any of immunoglobulin (Ig)G, IgA, IgM, IgE, and IgD. These antibodies may be polyclonal antibodies or monoclonal antibodies. These antibodies can be produced by a normal method using an animal such as a mouse, a rat, a goat, or a chicken.

Figure 9:
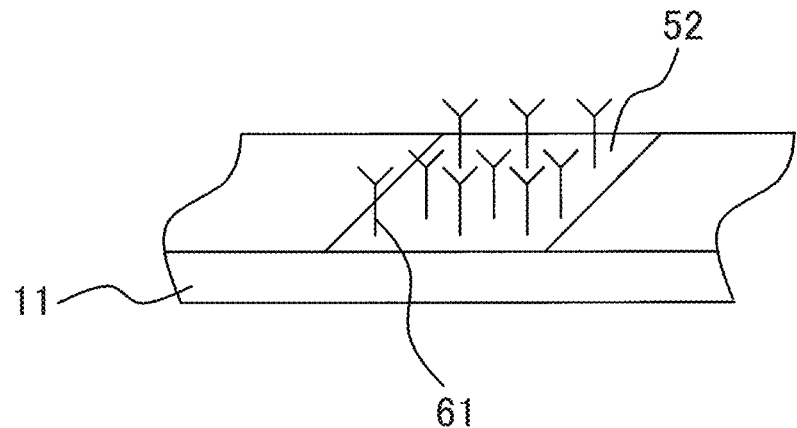
FIG. 9 is a schematic view illustrating antibodies immobilized on a detection portion in a detection instrument of Embodiment 1-2 according to the present invention.

FIG. 9 shows an example of immobilizing antibodies on the detection portion. As shown in FIG. 9, antibodies 61 are immobilized on a detection portion 52. FIG. 9 schematically shows the example, so that the size and the number of antibodies 61 are different from the actual size and the number. In FIG. 9, the numeral 11 indicates a main body of a detection instrument as shown in FIGS. 1A and 1B.

Next, a method for using the detection instrument of the present embodiment is described with reference to figures. The following method is a mere example, and the present invention is not limited to this.

First, a sample containing antibodies which have been labeled with an enzyme (hereinafter referred to as an "enzyme-labeled antibodies") and a chromogenic substrate corresponding to the enzyme of the enzyme-labeled antibodies are brought into contact with a detection portion 52.

The enzyme-labeled antibodies are not particularly limited as long as they bind to a detection object (antigen) in the sample and may be any of immunoglobulin (Ig)G, IgA, IgE, and IgD. These antibodies may be polyclonal antibodies or monoclonal antibodies. These antibodies can be produced by a normal method using an animal such as a mouse, a rat, a goat, or a chicken. The enzyme of the enzyme-labeled antibodies and the chromogenic substrate are not particularly limited and can be, for example, the same enzyme and the same chromogenic substrate as in Embodiment 1-1a.

When the sample contains the detection object (antigen), the detection object (antigen) and the enzyme-labeled antibodies are bound to each other by an antigen-antibody reaction.

Figure 10:
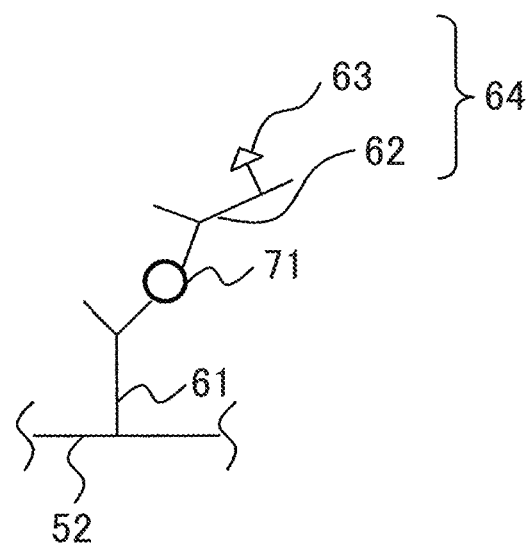
FIG. 10 is a schematic view illustrating the state of an antigen-antibody reaction in the detection instrument of Embodiment 1-2.

FIG. 10 schematically shows an antigen-antibody reaction in the present embodiment. In FIG. 10, the identical parts to those in FIG. 9 are denoted by identical reference numerals. As shown in FIG. 10, the detection object (antigen) 71 in a sample binds to antibodies 61 immobilized on the detection portion 52 as well as the enzyme-labeled antibodies 64, thus forming a complex. In FIG. 10, the numeral 62 indicates antibodies of the enzyme-labeled antibodies 64, and the numeral 63 indicates an enzyme of the enzyme-labeled antibodies 64. FIG. 10 schematically shows the antigen-antibody reaction, the sizes of the antibodies and a label and the like are different from the actual sizes and the like.

The detection object can be detected by detecting color development caused by a reaction of the enzyme of the enzyme-labeled antibodies and the chromogenic substrate in the detection portion 52 after predetermined time (not particularly limited and is, for example, from 10 to 20 minutes).

In the detection instrument of the present embodiment, a detection object in a sample may be an antibody, and an antigen for capturing the detection object (antibody) may be immobilized, as a detection reagent, on the detection portion. In this case, a sample containing antigen which has been labeled with an enzyme (hereinafter referred to as an "enzyme-labeled antigen") and a chromogenic substrate corresponding to the enzyme of the enzyme-labeled antigen is brought into contact with the detection portion 52.

In order to improve reliability of detection, it is preferred that a positive control which can be read optically is placed in the detection portion of the detection instrument according to the present invention.

Embodiment (2)

Figure 11:
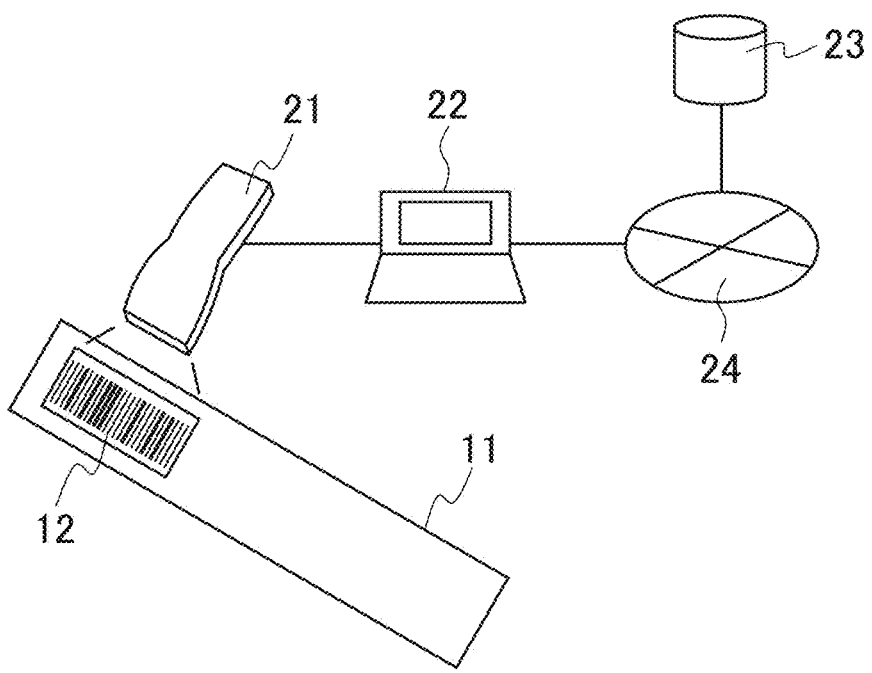
FIG. 11 is a schematic view showing an example of a configuration of a detection system of Embodiment 2 according to the present invention.

FIG. 11 shows an example of a configuration of a detection system according to the present invention. In FIG. 11, the identical parts to those in FIGS. 1A to 3D are denoted by identical reference numerals. As shown in FIG. 11, this detection system includes the detection instrument according to the present invention shown in FIG. 1A and an optical reader (bar-code reader) 21. The optical reader (bar-code reader) 21 is connected to a personal computer (PC) 22. The PC 22 is connectable to a server or a storage medium on a cloud system (hereinafter collectively referred to as a "server") 23 via a communication network or a cloud system (hereinafter collectively referred to as "communication network") 24. Examples of the communication network 24 include the Internet, and LAN (Local Area Network). The PC and the server are optional components, and the detection system according to the present invention is not required to have them.

In the present invention, the optical reader is not limited to a bar-code reader as long as it can read color development of the detection reagent in the detection instrument according to the present invention and can be, for example, a camera. For example, a camera integrated in a mobile phone can be used as the optical reader.

The method for using the detection system shown in FIG. 11 is as follows, for example. The following method, however, is a mere example, and the present invention is not limited by this.

First, a sample is brought into contact with a detection portion (bar code) 12. At that time, when a detection object is present in the sample, the detection reagent specifically reacts with the detection object and develops a color.

Then, the color development of the detection reagent in the detection instrument is read by an optical reader (bar-code reader) 21. This read result is displayed on the PC 22. That is, when color development of the detection reagent is read, a read result showing the presence of the detection object in the sample is displayed on the PC 22. On the other hand, when color development of the detection reagent is not read, a read result showing the absence of the detection object in the sample is displayed on the PC 22.

The read result may be stored in the server 23 via the communication network 24, and a next detection may be performed with reference to the read result. For example, in the case of using the detection system of the present embodiment in the production field of fermented food, when information on the presence or absence of color development and the extent of color development (color intensity) in the stages of preparation, the middle of fermentation, the end of fermentation is stored in the server 23, production of fermented food can be managed using the detection system of the present embodiment.

Embodiment (3)

Figure 12:
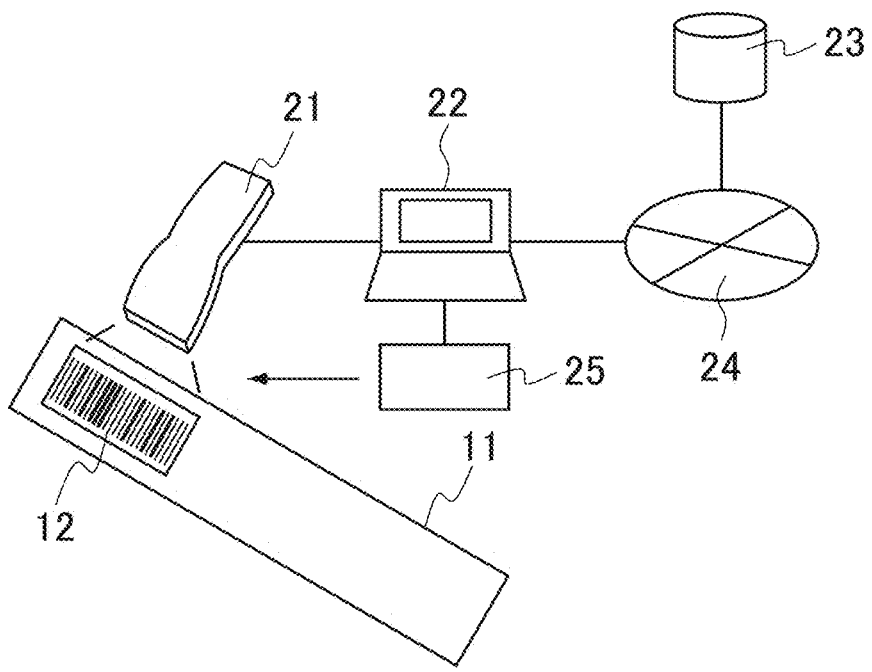
FIG. 12 is a schematic view showing an example of a configuration of a detection system of Embodiment 3 according to the present invention.

FIG. 12 shows another example of a configuration of the detection system according to the present invention. In FIG. 12, the identical parts to those in FIGS. 1A to 3D and 11 are denoted by identical reference numerals. As shown in FIG. 12, this detection system is the same as the detection system of Embodiment 2 shown in FIG. 11 except for including a printer (e.g., an ink jet recording device or a laser printer) 25 connected to a PC 22.

A method for using the detection system shown in FIG. 12 is as follows, for example. The following method, however, is a mere example, and the present invention is not limited by this.

First, a detection portion (bar code) 12 is formed in a main body 11 of a detection instrument with the printer 25. A specific method for forming the detection portion (bar code) 12 is the same as described in Embodiment 1. In the detection system of the present embodiment, when information has been already stored in the server 23, the detection portion (bar code) 12 may be formed with reference to the information stored in the server 23. Specifically, for example, in the case of using the detection system of the present embodiment in restaurants, hospitals, and the like, if information on seasonal increase and decrease of the number of microorganisms is stored in the server 23, the kind of the detection reagent may be changed according to the information in order to set microorganisms increased in the season of the detection as the detection object. Furthermore, for example, in the case where the detection system of the present embodiment is used in inspection of imported food, if information on a residual pesticide which has been detected from imported food in the past is stored in the server 23, the kind of the detection reagent may be selected according to the information in order to set the residual pesticide as the detection objects. The detection portion may be formed with reference to information on the Internet or a cloud system as substitute for the information stored in the server 23, for example.

Subsequently the detection object can be detected in the same manner as in Embodiment 2.

Embodiment (4)

Figure 13A:
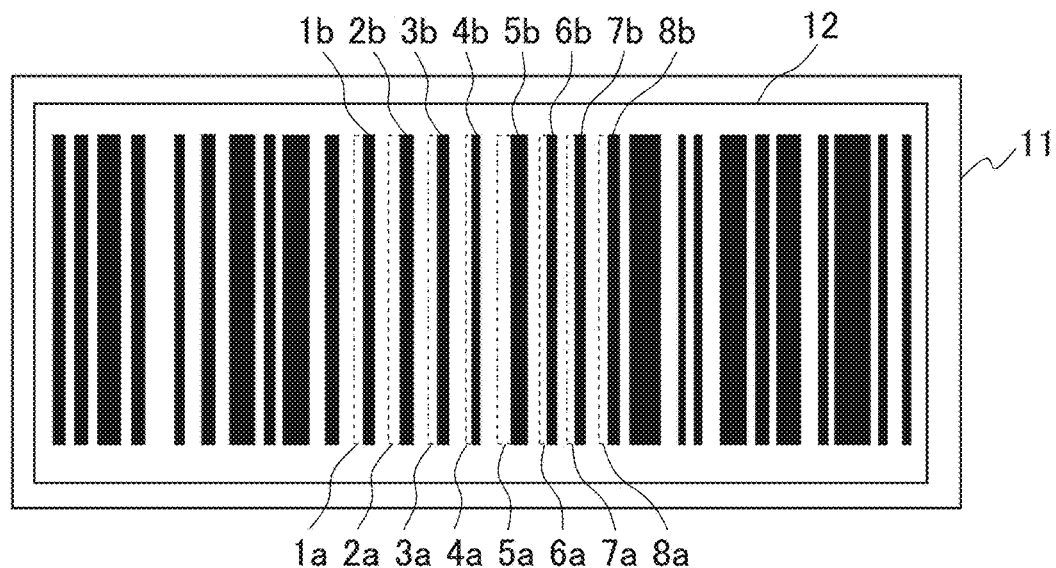
FIGS. 13A to 13C are views showing the respective detection instruments of Embodiments 4 to 6 according to the present invention.

The present embodiment is an example of a detection instrument configured so that a detection portion is formed in a main body. FIG. 13A shows a configuration of the detection instrument of the present embodiment. As shown in FIG. 13A, as the main body 11, a transparent and colorless plastic container is used. Moreover, a bar code is formed in the detection portion 12, and eight detection reagents 1a to 8a are placed as parts of the bar code. As the eight detection reagents 1a to 8a, reagents which develop a color by contact with the respective eight kinds of bacteria and virus are used. The detection reagents 1a to 8a are placed so as to be adjacent to the respective bars 1b to 8b in the detection portion (bar code) 12. Whether or not the eight kinds of bacteria and virus are present in the sample can be detected by reading whether or not the thicknesses of the bars 1b to 8b are increased after the contact.

Embodiment (5)

Figure 13B:
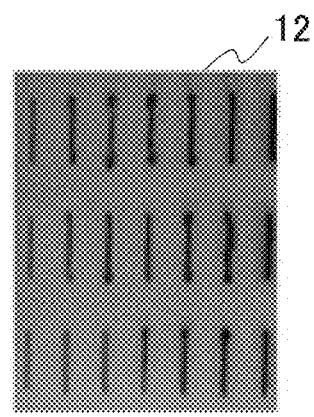

The present embodiment is an example of a detection instrument configured so that a detection reagent contains a nucleic acid element. As the nucleic acid element, a nucleic acid element containing a first nucleic acid portion and a second nucleic acid portion which is DNA (DNA enzyme) which can cause an enzyme reaction is used. FIG. 13B shows a configuration of the detection instrument of the present embodiment. As shown in FIG. 13B, the detection reagent (nucleic acid elements) containing a chromogenic substrate which develops a color by an enzyme reaction with the second nucleic acid portion is placed at 21 positions of a detection portion 12. The presence or absence of a detection object which releases the enzyme reaction from being inhibited by binding to the first nucleic acid portion in the sample can be detected from the presence or absence of color development of the detection reagent (nucleic acid element) at 21 positions caused by the contact of the sample with the detection portion 12.

Embodiment (6)

Figure 13C:
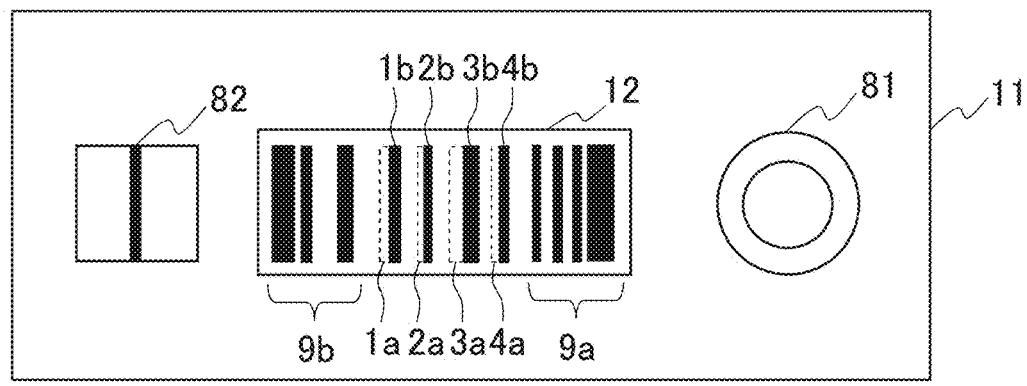

The present embodiment is an example of an immune chromatogram detection instrument configured so that a detection portion is formed in a main body thereof, and antibodies for capturing a detection object (antigens) are immobilized on the detection portion. FIG. 13C shows a configuration of a detection instrument of the present embodiment. As shown in FIG. 13C, a plate for development exerting capillary action is used as a main body 11. Moreover, a bar code is formed in the detection portion 12, and as parts of the bar code, four detection reagents 1a to 4a are placed in the same. As the four detection reagents 1a to 4a, the respective antibodies corresponding to the respective four kinds of bacteria and virus are used. The detection reagents 1a to 4a are placed so as to be adjacent to the respective bars 1b to 4b in the detection portion (bar code) 12. A part of the bar code 12 in which the detection reagents 1a to 4a are not placed includes information 9a on the detection reagents such as detection reagent numbers, and information 9b on a site at which detection is performed. Moreover, a sample supply portion 81 is formed on one side of the detection portion (bar code) 12 in the main body 11, and an antibody portion 82 for immobilization is formed on the other side of the same. Antibodies corresponding to any of the four kinds of bacteria and virus are immobilized on the antibody portion 82 for immobilization. A sample containing enzyme-labeled antibodies and a chromogenic substance corresponding to an enzyme of the enzyme-labeled antibodies are brought into contact with the sample supply portion 81, which is then stood still until color development of the antibody portion 82 for immobilization is detected. Thereafter, whether or not the thicknesses of the bars 1b to 4b are increased after the contact with the sample is read by a bar-code reader. Thus, the presence or absence of the four kinds of bacteria and virus in the sample can be detected with reference to information on the detection reagents such as detection reagent numbers and information on a site at which detection is performed.

INDUSTRIAL APPLICABILITY

The present invention provides a detection instrument and a detection system, by which everyone can easily detect an intended detection object without any skilled technique. The uses of the detection instrument and the detection system are not limited, and they are applicable in various fields such as food, medical cares, agriculture, and environment.

EXPLANATION OF REFERENCE NUMERALS

| | |
|---|---|
| 1 | detection instrument |
| 1a, 2a, 3a, 4a, 5a, 6a, 7a, 8a | detection reagent |
| 11 | main body |
| 12, 52 | detection portion (bar code) |
| 21 | optical reader (bar-code reader) |
| 22 | PC |
| 23 | server |
| 24 | communication network |
| 25 | printer |
| 31, 71 | detection object |
| 32, 42 | first nucleic acid portion |
| 33, 43 | second nucleic acid portion |
| 34 | labeling substance |
| 36, 46 | nucleic acid element |
| 61, 62 | antibody |
| 63 | enzyme |
| 64 | enzyme-labeled antibody |
| 81 | sample supply portion |
| 82 | antibody portion for immobilization |

The invention claimed is:

1. A detection method using a detection instrument, the detection instrument comprising:
   a detection portion, wherein
   a detection reagent which develops a color by specifically reacting with a detection object in a sample is placed in the detection portion,
   positional information of the detection reagent in the detection portion is information on the detection object,
   color development of the detection reagent can be optically read, and
   a bar code is formed in the detection portion, and
   wherein at least one of the following conditions is met:
   Condition (I): the detection reagent is placed on one to four positions of the barcode as a part of the bar code; and
   Condition (II): besides the bar code, the detection reagent is placed either on a part of or on the entire bar code, and the part of or the entire bar code is indistinguishable by color development of the detection reagent.

2. The method according to claim 1, wherein
   the detection reagent comprises a nucleic acid element,
   the nucleic acid element comprises a first nucleic acid portion and a second nucleic acid portion,
   the first nucleic acid portion is a binding portion which can bind to the detection object, the second nucleic acid portion is a labeling portion which can distinguish between binding and non-binding of the first nucleic acid portion and the detection object, and the labeling portion can cause the detection reagent to or not to develop a color according to the distinguishing between the binding and non-binding.

3. The method according to claim 2, wherein the detection reagent comprises a labeling substance, when the detection object does not bind to the first nucleic acid portion, the second nucleic acid portion can bind to the labeling substance, and when the detection object binds to the first nucleic acid portion, the second nucleic acid portion cannot bind to the labeling substance.

4. The method according to claim 3, wherein a secondary structure of the second nucleic acid portion changes by binding of the detection object to the first nucleic acid portion, and the labeling substance binding to the second nucleic acid portion is released from the second nucleic acid portion by the change of the secondary structure.

5. The method according to claim 4, wherein the labeling substance is an enzyme, the detection reagent contains a chromogenic substrate which develops a color by an enzyme reaction with the enzyme, when the enzyme binds to the second nucleic acid portion, the enzyme reaction with the enzyme is inhibited, and when the enzyme is released from the second nucleic acid portion, the enzyme reaction is released from being inhibited.

6. The method according to claim 2, wherein the second nucleic acid portion can cause an enzyme reaction, the detection reagent comprises a chromogenic substrate which develops a color by an enzyme reaction with the second nucleic acid portion, when the detection object does not bind to the first nucleic acid portion, the enzyme reaction with the second nucleic acid portion is inhibited, and when the detection object binds to the first nucleic acid portion, the enzyme reaction is released from being inhibited.

7. The method according to claim 2, wherein the first nucleic acid portion and the second nucleic acid portion are a single-stranded nucleic acid obtained by linking to each other.

8. The method according to claims 2, wherein the nucleic acid is RNA.

9. The method according to claims 2, wherein the first nucleic acid portion and the second nucleic acid portion are aptamers.

10. The method according to claim 1, wherein a positive control which can be read optically is placed in the detection portion.

\* \* \* \* \*